United States Patent [19]
Knifton et al.

[11] Patent Number: 5,811,620
[45] Date of Patent: Sep. 22, 1998

[54] USE OF REACTIVE DISTILLATION IN THE DEHYDRATION OF TERTIARY BUTYL ALCOHOL

[75] Inventors: John Frederick Knifton, Austin; John Ronald Sanderson, Leander; Melvin Ernest Stockton, Georgetown, all of Tex.

[73] Assignee: Huntsman Specialty Chemicals Corporation, Austin, Tex.

[21] Appl. No.: 657,118

[22] Filed: Jun. 3, 1996

Related U.S. Application Data

[60] Provisional application No. 60/011,517 Feb. 7, 1996.
[51] Int. Cl.[6] .................................. C07C 1/00; C07C 4/02
[52] U.S. Cl. ............................................. 585/639; 585/649
[58] Field of Search ............................ 568/840; 585/639, 585/649; 502/64, 85, 80

[56] References Cited

U.S. PATENT DOCUMENTS

| | | |
|---|---|---|
| 4,306,106 | 12/1981 | Kerr et al. . |
| 4,547,601 | 10/1985 | Holland et al. . |
| 4,967,020 | 10/1990 | Marler et al. . |

*Primary Examiner*—Gary Geist
*Assistant Examiner*—Karl J. Puttlitz, Jr.
*Attorney, Agent, or Firm*—Russell R. Stolle; Carl G. Ries

[57] ABSTRACT

A tertiary butyl alcohol feedstock is dehydrated to form isobutylene and water in a reactive distillation column having a reactive distillation section in the middle portion thereof containing a bed of a TBA dehydration catalyst and a substantially anhydrous lower boiling isobutylene fraction is recovered adjacent the top of the reactive distillation column and a higher boiling aqueous fraction is recovered adjacent the bottom of the reactive distillation column.

8 Claims, 1 Drawing Sheet

USE OF REACTIVE DISTILLATION IN THE DEHYDRATION OF TERTIARY BUTYL ALCOHOL

This application claims the benefit of U.S. Provisional Application Number 60/011,517 filed Feb. 7, 1996.

BACKGROUND OF THE INVENTION

1. Technical Field of the Invention

This invention relates to a process for the manufacture of isobutylene (IBTE) from tertiary butyl alcohol (TBA). More particularly, this invention relates to the catalytic reactive distillation of tertiary butyl alcohol (TBA) in order to substantially quantitatively convert the TBA to isobutylene and water and to substantially simultaneously separate the isobutylene and water from the TBA to obtain a high yield of substantially anhydrous isobutylene (IBTE). Still more particularly, this invention relates to a process for the manufacture of IBTE from TBA wherein by-product water formed by the dehydration of TBA is substantially separated from the IBTE as formed to provide a high yield of a substantially anhydrous distillate IBTE distillation/reaction product and wherein contaminating quantities of water are removed, by distillation, substantially as formed to provide a separate reaction/distillation fraction.

Isobutylene is useful as a raw material for the manufacture of methyl tertiary butyl ether, ethyl tertiary butyl ether, etc, as well as in the manufacture of polyisobutylenes.

2. Prior Art

Smith U.S. Pat. No. 4,215,011 discloses a reactive distillation column having both a catalytic function and a distillation function that is useful, for example, in the polymerization of butene.

In Smith U.S. Pat. No. 4,232,177 a method for conducting chemical reactions in a reactive distillation column is disclosed wherein a reaction mixture is fed to a reactive distillation column and contacted with a fixed bed catalytic packing to concurrently carry out the reaction and to fractionate the reaction mixture.

Various types of catalytic packing that can be used in a reactive distillation column are disclosed in Smith U.S. Pat. No. 4,443,559.

Smith U.S. Pat. No. 5,118,873 discloses a process wherein isobutylene and methanol are reacted in the presence of an acid cation exchange resin to form MTBE and concurrently fractionated to provide an overhead fraction comprising unreacted isobutylene and unreacted methanol and a bottoms fraction comprising methyl tertiary butyl ether and contaminants.

Matouq et al. discuss a "COMBINED PROCESS FOR PRODUCTION OF METHYL TERT.-BUTYL ETHER FROM TERT.-BUTYL ALCOHOL AND METHANOL" in *Journal of Chemical Engineering of Japan*, Vol. 27, No. 3, 1994, pp. 301–306.

Another discussion on the formation of methyl tertiary butyl ether is found in a paper entitled "WHY METHYL TERT.-BUTYL ETHER PRODUCTION BY REACTIVE DISTILLATION MAY YIELD MULTIPLE SOLUTIONS," *Ind. Eng. Chem. Res.* 1995, Vol. 34, pp. 987–991.

A study of the dehydration of tertiary butyl alcohol is disclosed in an article by Ohtsuka et al. entitled "STUDIES OF THE ACIDITY AND IONIC CONDUCTIVITY OF SILICA-SUPPORTED HETEROPOLY COMPOUNDS. I. THE DEHYDRATION OF t-BUTYL ALCOHOL OVER HETEROPOLY COMPOUND CATALYSTS," *Bull. Chem. Soc. Jpn.*, Vol. 62, 3195–3201 (1989).

The manufacture of isobutylene by the dehydration of tertiary butyl alcohol is also discussed by Abraham et al. in a paper entitled "MAKE ISOBUTYLENE FROM TBA," *Hydrocarbon Processing*, Feb. 1992, pp. 51–54.

Another paper discussing the dehydration of tertiary olefins by Kantam et al. is entitled "MONTMORILLONITE CATALYZED DEHYDRATION OF TERTIARY ALCOHOLS TO OLEFINS" is found in the *Tetrahedron Letters*, Vol. 34, No. 7, pp. 1185–1186 (1993).

SUMMARY OF THE INVENTION

In accordance with the present invention, tertiary butyl alcohol is charged to a reactive distillation column having a reaction distillation section therein containing a tertiary butyl alcohol dehydration catalyst. The tertiary butyl alcohol is dehydrated therein to form a higher boiling water fraction for withdrawal adjacent the bottom of the tower and a lower boiling fraction comprising isobutylene for upward flow to form a lower boiling isobutylene fraction for withdrawal adjacent the top of the tower. The water formed in the reactive distillation section will flow downwardly for recovery as a higher boiling water fraction and the isobutylene will flow upwardly through the reactive distillation column as a substantially anhydrous isobutylene fraction.

DETAILED DESCRIPTION OF THE PRESENT INVENTION

This invention relates to an improvement in a process for the manufacture of isobutylene from tertiary butyl alcohol wherein tertiary butyl alcohol is dehydrated in a reactive distillation column in the presence of a tertiary butyl alcohol dehydration catalyst to provide a dehydration reaction product comprising isobutylene and water and wherein the dehydration product is separated in the reactive distillation column into a lower boiling distillation fraction comprising isobutylene and a higher boiling distillation fraction comprising water.

In greater detail, this invention relates to an improvement in a process for the manufacture of isobutylene (IBTE) from tertiary butyl alcohol (TBA) which comprises:

Continuously charging a feed comprising TBA to a reactive distillation column containing a bed of a TBA dehydration catalyst to dehydrate the TBA to form water and IBTE and to provide a higher boiling reactive distillation water fraction for withdrawal adjacent the bottom of the tower and a lower boiling fraction comprising IBTE for recovery adjacent the top of the tower.

The Tertiary Butyl Alcohol Dehydration Catalyst

In accordance with the IBTE manufacture and purification method of the present invention, a reactive distillation column is provided which contains a bed of a tertiary butyl alcohol dehydration catalyst. A wide variety of tertiary butyl alcohol dehydration catalysts can be used for this purpose, but particularly alumino-silicate zeolites and clays such as, for example, beta-type zeolites, fluoride-treated beta zeolite catalysts, fluoride-treated clay catalysts, etc. A preferred catalyst is a HF treated beta zeolite catalyst.

Zeolites are disclosed in Japanese Patent 0007432 and aluminosilicate zeolites as disclosed in Chang et al. U.S. Pat. No. 4,058,576 may also be used.

The reaction conditions to be utilized when dehydrating tertiary butyl alcohol in the presence of a tertiary butyl alcohol dehydration catalyst of the type disclosed in the prior art include a reaction temperature of about 200° to about 315° C., in combination with a pressure of about 20 to about 110 psia (see Abraham et al., *Hydrocarbon*

*Processing*, February 1992, pp. 51–54, cited above). Typical alcohol dehydration catalysts used in the prior art include alumina or alumina impregnated with silica. Also useful are cation exchange resins and p-toluene sulfonic acid. See, for example, U.S. Pat. Nos. 3,665,048 (1972), 4,155,945 (1979), 4,165,343 (1979), and 4,208,540 (1980).

Particularly useful as catalysts for the dehydration of tertiary butyl alcohol via reactive distillation in the practice of this invention are the crystalline aluminosilicate beta zeolites. Zeolite beta was first synthesized at the Mobil Research Laboratories; its composition is described in U.S. Pat. Nos. 3,308,069, 4,419,220, 4,518,485, and 4,740,292. Zeolite beta is a crystalline aluminosilicate having a pore size greater than 5 angstroms, in its synthesized form. Its composition may be expressed as follows:

$$[XNa(1.0\pm0.1-X)TEA]AlO_2 \cdot YSiO_2 \cdot WH_2O$$

where X is less than 1, preferably less than 0.7; TEA represents the tetraethyl ammonium ion; Y is greater than 5 but less than 100; and W is up to about 60 (it has been found that the degree of hydration may be higher than originally determined, where W was defined as being up to 4), depending on the degree of hydration and the metal cation present. The TEA component is calculated by differences from the analytical value of sodium and the theoretical cation to structural aluminum ratio of unity.

The preferred forms of zeolite beta are the highly acidic, high silica forms, having silica-to-alumina mole ratios of at least 10:1, and most preferably having silica-to-alumina mole ratios in the range of 20:1 to 100:1. The silica-to-alumina ratios referred to in this specification are the structural or framework ratios; that is, the ratio of the $SiO_4$ to the $AlO_4$ tetrahedral, which together constitute the structure by which the zeolite is composed.

A second preferred form of acidic zeolite catalyst for the dehydration of tertiary aliphatic alcohols, such as tertiary butyl alcohol, are fluoride-modified beta zeolites. Suitable fluoride-containing agents for treating said beta zeolites and dealuminized beta zeolites include hydrogen fluoride, hydrofluoric acid, fluorophosphoric acids such as monofluorophosphoric acid and difluorophosphoric acid, as well as ammonium fluoride, fluorosulfonic acids such as trifluoromethane sulfonic acid and its congeners, and triflic anhydride.

Hydrogen fluoride or hydrofluoric acid are the preferred fluoriding agents. The hydrogen fluoride-modified zeolite is typically prepared by treating the beta zeolite or dealuminized beta zeolite with an aqueous solution of hydrofluoride acid. Said aqueous solution of hydrofluoric acid should be greater than 0.1N and preferably from about 0.5 to 5N. After treatment the zeolite is recovered by filtration or decantation, washed with distilled water, dried and calcined. Typical calcination temperatures are in the range of 300° to 600° C.

The fluoride-treated beta zeolite should have a fluoride content of at least 0.1%. The preferred fluoride content for said fluoride-treated beta zeolites useful for tertiary alcohol dehydration via reactive distillation is 0.5 to 10 weight percent.

Said beta zeolites or modified beta zeolites may be in the form of powders, pellets, granules, spheres, shapes and extrudates. The examples described herein demonstrate the advantages of using extrudates.

A further class of catalysts useful for the dehydration of tertiary aliphatic alcohol, such as tertiary butyl alcohol, are silica-alumina clays. Chemically, clays are composed primarily of silicon, aluminum and oxygen, with minor amounts of magnesium and iron in some cases. Variations in the ratios of these constituents, and their crystal lattice configurations, results in some fifty separate clays, each with its own characteristic properties.

Particularly effective in t-butanol dehydration are smectite clays. These three-layered sheet clay structures include montmorillonite, vermiculite, and some brittle mica. A general representation of the montmorillonite structure is:

$$M_{x/n}{}^{n+} \cdot yH_2O(Al_{4-x}M_{9x})(Si_8)O_{20}(OH)_4$$

where M represents the interlamellar (balancing) cations, normally sodium or lithium, and x, y, and n are integers. The clay components of the catalysts used in the present invention may comprise neutral or acidic clays, particularly mineral acid-treated clays, having a surface area of greater than 30 $m_2/g$ and a moisture content in the range from zero to 20 wt. %.

Fluoride-treated clays useful for t-butanol dehydration are normally prepared by treating said montmorillonite clay structure with a fluoride agent selected from the group including hydrogen fluoride, hydrofluoric acid, fluorophosphoric acids such as monofluorophosphoric acid and difluorophosphoric acid, ammonium fluoride, fluorosulfonic acids such as trifluoromethane sulfonic acid and its congeners, and triflic anhydride. Said fluoride-treated clays should have a fluoride content after treatment of at least 0.1%, and preferably a fluoride content in the range of 0.2 to 2 weight percent.

Said clays may be in any physical form, but the subsequent examples illustrate fluoride-treated clays in granular form.

The Reactive Distillation Column

In accordance with the present invention, a feedstock comprising tertiary butyl alcohol is brought into contact with a bed of a tertiary butyl alcohol dehydration catalyst, as described above, in a reactive distillation column in order to convert a significant portion of the TBA to isobutylene and water.

The reactive distillation column to be used in accordance with the present invention is a reactive distillation column of the type disclosed in the Smith patents referenced above. The reactive distillation column of the present invention will comprise an intermediate or central reactive distillation section to which the tertiary butyl alcohol feedstock is charged for processing, plus upper and lower distillation sections.

The tertiary butyl alcohol feedstock will normally contain from about 90 to about 98 wt. % of tertiary butyl alcohol and impurities including from about 0.05 to about 2 wt. % of water, from about 0.1 to about 2 wt. % of methanol and minor amounts (e.g., less than 1 wt. % each) of contaminants including isobutylene, diisobutylene, methyl tertiary butyl ether, acetone, isopropanol, t-butyl formate, di-t-butyl peroxide, etc. Other tertiary aliphatic alcohols may also be useful feedstocks in the practice of this invention, such as tertiary amyl alcohol.

The tertiary butyl alcohol feedstock is charged to the intermediate reactive distillation section under reaction conditions, as described above, where it is dehydrated to form an isobutylene reaction product comprising isobutylene, water and impurities. The lower boiling components of the dehydration product, including isobutylene and lower boiling impurities will flow upwardly from the intermediate reactive distillation section to the upper distillation section where the IBTE is recovered adjacent the top of the reactive distillation column as a lower boiling distillation isobutylene reaction product. The higher boiling components of the dehydration product, including water and higher boiling impurities will flow downwardly from the intermediate reactive distillation section to the lower distillation section where the water is recovered adjacent the bottom of the reactive distillation column as a higher boiling aqueous distillation reaction product.

DESCRIPTION OF THE PREFERRED EMBODIMENT

Figure 1:
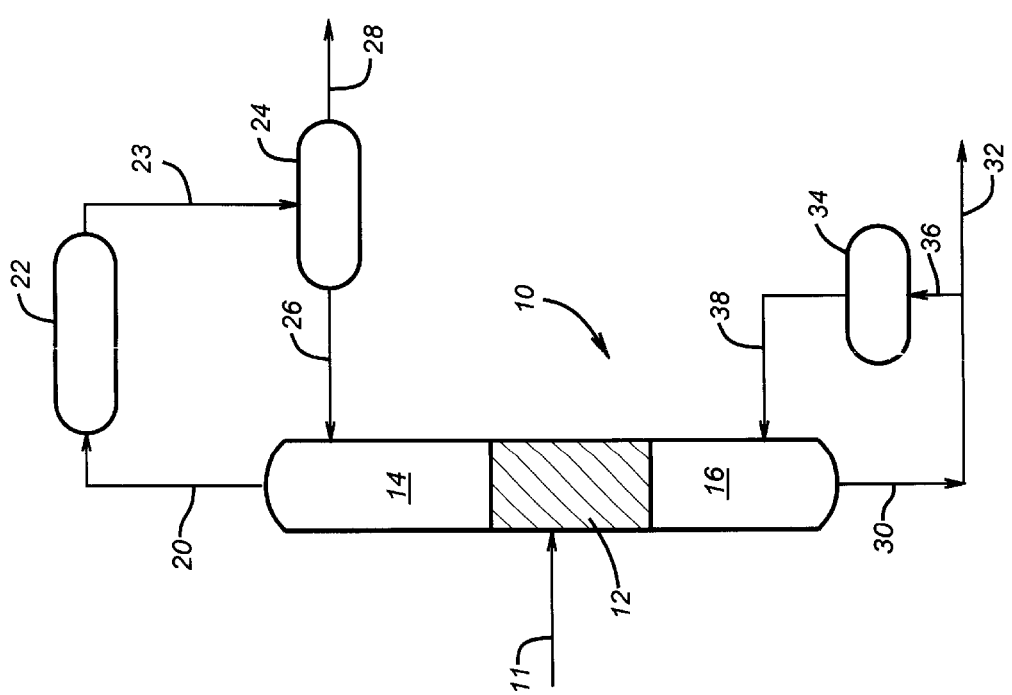
FIG. 1 is a general schematic flow sheet with conventional parts omitted showing the normal reaction and recovery sequence of the present invention for the manufacture of isobutylene.

Turning now to FIG. 1, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condensers, reboilers, etc., have been omitted.

In accordance with the present invention, a tertiary butyl alcohol feedstock is charged to a reactive distillation column 10 having a reaction distillation section 12 containing a bed of a tertiary butyl alcohol dehydration catalyst.

The tertiary butyl alcohol in the feedstock is dehydrated in the reaction distillation section 12 to form an isobutylene reaction product comprising isobutylene and impurities. The lower boiling components of the dehydration product, including isobutylene will flow upwardly from the intermediate reactive distillation section to an upper distillation section 14 where the lower boiling components are withdrawn as a lower boiling distillation isobutylene reaction product by a line 20 leading to a condenser 22 where the lower boiling components are liquified. The liquified lower boiling distillation fraction 20 is passed by a line 23 to an accumulator 24 from which reflux is returned to the reactive distillation column 10 adjacent the top thereof by a line 26. Product isobutylene is withdrawn from the accumulator 24 by an isobutylene draw-off line 28.

The higher boiling components of the dehydration product, including water and higher boiling impurities will flow downwardly from the intermediate reactive distillation section 12 to a lower distillation section 16 where the water is recovered adjacent the bottom of the reaction distillation column 10 as a higher boiling aqueous distillation reaction product 30. A portion of the higher boiling aqueous distillation reaction product 30 is withdrawn from the system by a draw-off line 32 and the remainder of the higher boiling aqueous distillation reaction product 30 is charged to a reboiler 34 by a line 36 where it is heated to a desired reboiler temperature and then returned to the reactive distillation column 10 adjacent the bottom thereof by a reboiler line 38.

Distillation conditions that may be used in the reactive distillation column 90 may suitably include a column temperature range of about 30° to about 150° C., and more preferably from about 60° to about 120° C., a reboiler temperature of about 50° to about 180° C., and more preferably from about 70° to about 140° C., and a pressure of about zero to about 500 psi, and more preferably from about 5 to about 30 psi.

EXAMPLES

The invention will be further illustrated by the following specific examples, which are given by way of illustration and not as limitations on the scope of the invention. Where parts are mentioned, they are parts by weight.

Figure 2:
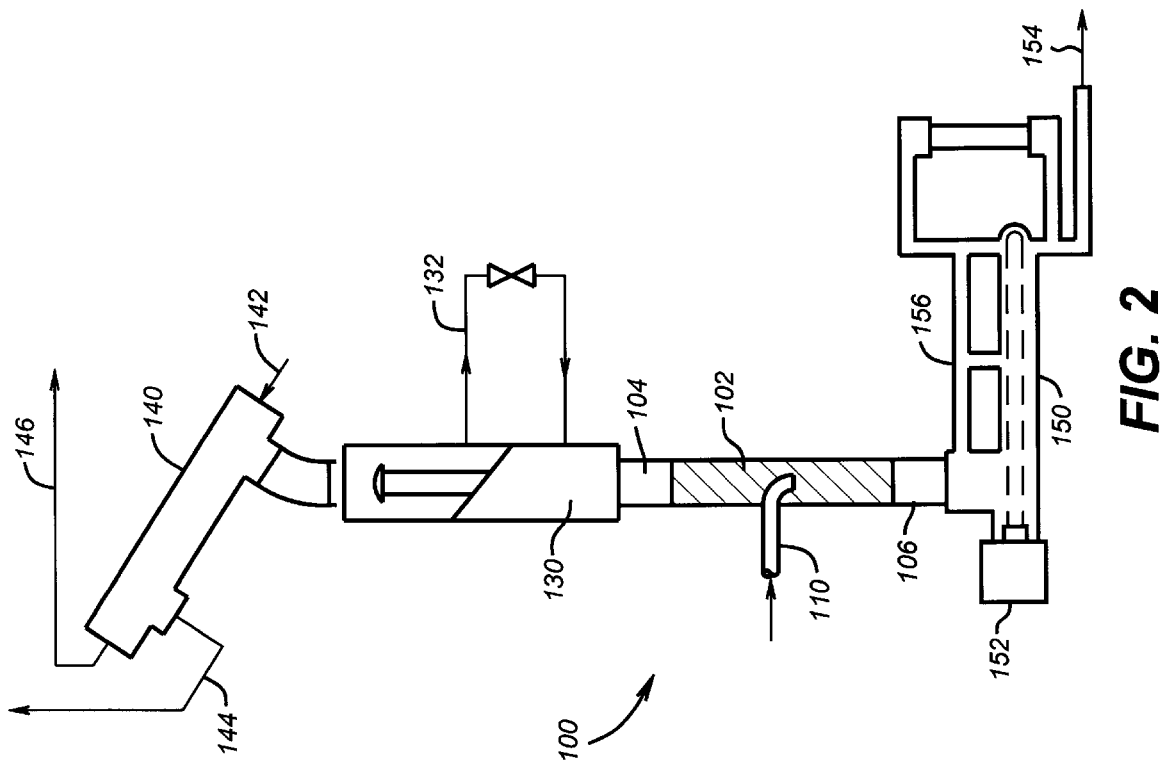
FIG. 2 is a plan view of a reactive distillation column useful for pilot plant studies.

The experiments described herein were conducted in a pilot unit reactive distillation column of the type shown in FIG. 2. The pilot unit comprised a reactive distillation column 100 containing a bed 102 of an isobutylene dehydration catalyst, an upper distillation section 104 containing a distillation packing (e.g., Goodloe packing) and a lower distillation section 106, also containing distillation packing. The tertiary butyl alcohol feedstock was charged to the bed 102 by a feed line 110.

The lower boiling distillation isobutylene reaction product components flow upwardly through the upper distillation section 104 to a reflux splitter 130 and then to a reflux condenser 140 where the lower boiling distillation isobutylene reaction product is cooled by water flowed through the reflux condenser 140 by a water charge line 142 and a water discharge line 144. The product isobutylene is withdrawn by a line 146.

Reflux is recirculated within the reflux splitter 130 withdrawn by a reflux line 132.

The higher boiling aqueous distillation reaction product flows downwardly through the lower distillation section 106 to a reboiler 150 where it is heated by an electrical heater 152. A portion of the higher boiling aqueous distillation reaction product 150 is withdrawn by a line 154 and the remainder of the higher boiling aqueous distillation reaction product is returned to the reactive distillation column 100 by a reboiler return line 156.

The attached Examples 1–3 illustrate t-butanol dehydration to isobutylene in the reactive distillation unit of FIG. 2 where, in the presence of zeolite beta, under moderate pressures (0–20 psi) and temperatures (<130° C.), quantitative t-butanol conversion levels are achieved with simultaneous separation of the isobutylene and water fractions as overhead and bottoms products in good selectivities (see Tables 1, 2, and 3). Crude (95%) t-butanol may be used here as a suitable feedstock, containing measurable quantities of water, methanol (MeOH), isobutylene ($C_4H_8$), acetone ($AC_2O$), methyl t-butyl ether (MTBE) and methyl ketone (MEK).

In Example 4, a similar t-butanol dehydration to isobutylene is illustrated using an HF-treated montmorillonite clay catalyst.

In Example 5, t-butanol dehydration is effected using a HF-treated beta zeolite catalyst, again with simultaneous separation of the isobutylene and water coproducts.

In Examples 6–31, t-butanol dehydration is effected with two beta zeolite catalysts over a range of mild operating conditions.

EXAMPLES 1–3 (7393-6 and -8)

These examples illustrate the dehydration of tertiary-butanol using reactive distillation equipment and zeolite catalysts.

t-Butanol dehydration was conducted using the equipment of FIG. 2 comprising a reactive distillation column, a reboiler, condenser, pressure and temperature controls, plus feed inlet, as well as heavy and lights product recovery capabilities.

To the reactive distillation column was charged 350 cc of zeolite beta having a silica-to-alumina mole ratio of 24 and a surface area of 630–650 $m_2$/g (80% beta, 20% alumina binder) as 1/16" diameter extrudates. The reboiler was filled with aqueous t-butanol, then crude t-butanol (ca. 95%) was continuously charged to the middle of the column, as shown in FIG. 2, at a rate of ca. 100 cc/hr. The liquid in the reboiler was slowly brought to reflux under 10 psi pressure and product taken off both as overhead lights (T) and as a bottoms fraction (B).

Under steady state conditions, samples of both the overhead and bottoms were collected and analyzed by glc. with a reboiler temperature of 110° C. and a column temperature range of 64°–99° C., a sample (362 g) of overhead product was found to comprise ca. 94% isobutylene. A full analysis may be found in Table 1. The corresponding bottoms product fraction (142 g) was found to be 97% water, containing only 0.2% unreacted t-butanol. Again, analytical details may be found in Table 1.

A second experimental run where the reactive distillation unit was operated under 20 psi pressure and the column and reboiler temperatures were 50°–105° C. and 127° C., respectively, gave very similar results—see Table 2. Here again, the light product fraction comprised ca. 81% isobutylene, while the bottoms liquid was ca. 97% water. t-Butanol conversion was once more close to quantitative.

EXAMPLE 4 (7394-5)

This example illustrates the dehydration of tertiary-butanol using reactive distillation equipment and an HF-treated clay catalyst.

t-Butanol dehydration was conducted using the equipment and procedures of Example 1. The reactive distillation column was charged with 300 cc of 0.6% HF-treated montmorillonite clay granules (20/60 mesh). The reboiler was filled with aqueous t-butanol and the crude t-butanol feed of Example 1 was continuously charged to the middle of the column as shown in FIG. 2 at a rate of ca. 100 cc/hr.

Under steady state conditions, with a reboiler temperature of 78° C. and a column temperature range of 37°–83° C., a sample of overhead product showed the presence of significant quantities of isobutylene.

EXAMPLE 5 (7393-14)

This example illustrates the dehydration of tertiary butanol using reactive distillation equipment and an HF-treated beta zeolite catalyst.

TABLE 1 t-Butanol Dehydration - Beta Zeolite Catalyst

| | Percentage (%)[a] | | | | | | |
|---|---|---|---|---|---|---|---|
| | $H_2O$ | MeOH | $C_4H_8$ | $AC_2O$ | TBA | MTBE | $C_8H_{16}$ |
| Feed composition | 1.3 | 0.5 | 0.1 | 1.6 | 94.7 | 0.4 | |
| Product-Lights fraction | 0.1 | | 94.4 | 1.6 | | 2.2 | 0.2 |
| Product-Bottoms fraction | 97.2 | | | | 0.2 | 1.4 | 0.6 |

[a]Abbreviations: Methanol (MeOH), Isobutylene ($C_4H_8$), Acetone ($AC_2O$), t-butanol (TBA), methyl t-butyl ether (MTBE), diisobutylene ($C_8H_{16}$).

TABLE 2 t-Butanol Dehydration - Beta Zeolite Catalyst

| | Percentage (%) | | | | | | |
|---|---|---|---|---|---|---|---|
| | $H_2O$ | MeOH | $C_4H_8$ | $AC_2O$ | TBA | MTBE | $C_8H_{16}$ |
| Feed composition | 1.3 | 0.5 | 0.1 | 1.6 | 94.7 | 0.4 | |
| Product-Lights fraction | 0.2 | 0.1 | 80.7 | 0.9 | | 5.1 | 12.4 |
| Product-Bottoms fraction | 96.5 | | | | 0.3 | 1.9 | 0.7 |

A third experimental run, where the reactive distillation unit was operated with zeolite beta catalyst at atmospheric pressure again provided both overhead and bottoms product. With the column and reboiler temperatures set at 70°–80° C. and 78° C., respectively, typical results are summarized in Table 3.

t-Butanol dehydration was conducted using the equipment and procedures of Example 1. The reactive distillation column was charged with 350 cc of 5.7% HF-treated beta zeolites, as 1/16" extrudates. The reboiler was filled with aqueous t-butanol and the crude t-butanol of Example 1 was

TABLE 3 t-Butanol Dehydration - Beta Zeolite Catalyst

| | Percentage (%) | | | | | | |
|---|---|---|---|---|---|---|---|
| | $H_2O$ | MeOH | $C_4H_8$ | $AC_2O$ | TBA | MTBE | $C_8H_{16}$ |
| Feed composition | 1.3 | 0.5 | 0.1 | 1.6 | 94.7 | 0.4 | |
| Product-Lights fraction | 5.6 | 0.4 | 55.9 | 1.2 | 34.1 | 0.8 | 0.6 |
| Product-Bottoms fraction | 19.0 | | | | 76.1 | 0.1 | 0.7 | continuously charged to the middle of the column as shown in FIG. 2 at the rate of ca. 100 cc/hr.

Under steady state conditions, with a reboiler temperature of 112° C. and a column temperature range of 87°–96° C., typical results are summarized in Table 4.

TABLE 4 t-Butanol Dehydration - HF/Beta Zeolite

| | Percentage (%) | | | | | | |
|---|---|---|---|---|---|---|---|
| | $H_2O$ | MeOH | $C_4H_8$ | $AC_2O$ | TBA | MTBE | $C_8H_{16}$ |
| Feed composition | 1.3 | 0.5 | 0.1 | 1.6 | 94.7 | 0.4 | |
| Product-Lights fraction | 1.3 | 0.5 | 59.9 | 10.7 | 12.7 | 10.3 | 1.2 |
| Product-Bottoms fraction | 95.3 | | | | 0.7 | 1.8 | 1.2 |

EXAMPLES 6–15

These examples illustrate the use of a beta zeolite catalyst (from PQ Corp., having a silica-to-alumina mole ratio of 24, in 1/16" diameter extruded form) where t-butanol conversion per pass is up to 96% (Example 7) under mild column temperatures of less than 100° C. Again, the isobutylene is taken off as an overhead fraction in up to 94% purity, while water plus unreacted TBA comprise the principal components of the bottoms take-off liquid.

Data are summarized in Tables 5-1 through 5-5.

TABLE 5-1 tert-Butyl Alcohol Dehydration by Catalytic Distillation

| | 7456-7 | | | 7456-8 | | |
|---|---|---|---|---|---|---|
| | Feed | Bottoms | Traps | Feed | Bottoms | Traps |
| Water | 1.345 | 66.746 | 0.320 | 1.345 | 62.245 | 0.275 |
| Methanol | 0.366 | 0.039 | 0.133 | 0.366 | 0.000 | 0.065 |
| Isobutylene | 0.000 | 0.000 | 93.694 | 0.000 | 0.000 | 93.160 |
| Acetone | 1.364 | 0.850 | 1.595 | 1.364 | 0.046 | 2.294 |
| Isopropanol | 0.324 | 0.387 | 0.044 | 0.324 | 0.567 | 0.026 |
| t-Butyl Alcohol | 94.918 | 30.032 | 2.829 | 94.918 | 34.595 | 2.443 |
| Me-t-Butyl Ether | 0.050 | 0.558 | 1.150 | 0.050 | 0.195 | 1.607 |
| Me Et. Ketone | 0.169 | 0.941 | 0.087 | 0.169 | 1.312 | 0.000 |
| Diisobutylene | 0.061 | 0.000 | 0.000 | 0.061 | 0.451 | 0.000 |
| Unknowns | 1.403 | 0.447 | 0.148 | 1.403 | 0.589 | 0.130 |
| Weight (g) | 329.0 | 141.0 | 269.0 | 616.0 | 33.0 | 513.0 |
| Reactor Conditions: | | | | | | |
| Reboiler Temp., (°C.) | 99 | | | 99 | | |
| Column Bottom, Temp., (°C.) | 98 | | | 98 | | |
| Column Top, Temp., (°C.) | 50 | | | 67 | | |
| Reflux Temp., (°C.) | 34 | | | 46 | | |
| Differential Press. (In.) | 0 | | | 0 | | |
| Reactor Press., (psig) | 10.7 | | | 9.6 | | |
| Feed Rate, (g/hr) | 103 | | | 108 | | |
| Time on Stream (Hr) | 4.2 | | | 6.0 | | |
| Catalyst | Valfor CP 861 DL-25 (B-Zeolite) | | | Valfor CP 861 DL-25 (B-Zeolite) | | |
| Material Balance, % | 124.62 | | | 88.64 | | |
| t-Butyl Alcohol Conversion, % | 84.00 | | | 95.90 | | |
| Isobutylene Selectivity, % | 126.94 | | | 112.60 | | |
| Water Selectivity, % | 142.01 | | | 10.03 | | |
| Diisobutylene Selectivity, % | −0.05 | | | −0.03 | | |

TABLE 5-2 tert-Butyl Alcohol Dehydration by Catalytic Distillation

|  | 7456-9 | | | 7456-10 | | |
| --- | --- | --- | --- | --- | --- | --- |
|  | Feed | Bottoms | Traps | Feed | Bottoms | Traps |
| Water | 1.345 | 77.825 | 0.000 | 1.890 | 59.870 | 0.210 |
| Methanol | 0.366 | 0.000 | 0.043 | 0.355 | 0.061 | 0.061 |
| Isobutylene | 0.000 | 0.000 | 93.340 | 0.000 | 0.000 | 90.416 |
| Acetone | 1.364 | 0.018 | 1.746 | 1.249 | 0.097 | 2.778 |
| Isopropanol | 0.324 | 0.508 | 0.038 | 0.323 | 0.657 | 0.079 |
| t-Butyl Alcohol | 94.918 | 18.746 | 3.170 | 94.540 | 37.756 | 3.709 |
| Me-t-Butyl Ether | 0.050 | 0.216 | 1.312 | 0.056 | 0.214 | 2.310 |
| Me Et. Ketone | 0.169 | 1.061 | 0.000 | 0.157 | 1.131 | 0.000 |
| Diisobutylene | 0.061 | 0.899 | 0.080 | 0.000 | 0.000 | 0.162 |
| Unknowns | 1.403 | 0.727 | 0.271 | 1.430 | 0.214 | 0.275 |
| Weight (g) | 843.0 | 95.0 | 549.0 | 1118.0 | 533.0 | 481.0 |
| Reactor Conditions: | | | | | | |
| Reboiler Temp., (°C.) | 99 | | | 96 | | |
| Column Bottom, Temp., (°C.) | 97 | | | 95 | | |
| Column Top, Temp., (°C.) | 72 | | | 53 | | |
| Reflux Temp., (°C.) | 51 | | | 43 | | |
| Differential Press. (In.) | 0 | | | 0 | | |
| Reactor Press., (psig) | 8.3 | | | 7.8 | | |
| Feed Rate, (g/hr) | 146 | | | 195 | | |
| Time on Stream (Hr) | 6.0 | | | 5.0 | | |
| Catalyst | Valfor CP 861 DL-25 (B-Zeolite) | | | Valfor CP 861 DL-25 (B-Zeolite) | | |
| Material Balance, % | 76.39 | | | 90.70 | | |
| t-Butyl Alcohol Conversion, % | 95.60 | | | 79.27 | | |
| Isobutylene Selectivity, % | 88.51 | | | 68.58 | | |
| Water Selectivity, % | 33.67 | | | 146.81 | | |
| Diisobutylene Selectivity, % | 0.075 | | | 0.06 | | |

TABLE 5-3 tert-Butyl Alcohol Dehydration by Catalytic Distillation

|  | 7456-11 | | | 7456-14 | | |
| --- | --- | --- | --- | --- | --- | --- |
|  | Feed | Bottoms | Traps | Feed | Bottoms | Traps |
| Water | 1.437 | 35.397 | 0.859 | 1.562 | 38.555 | 1.643 |
| Methanol | 0.367 | 0.000 | 0.000 | 0.325 | 0.099 | 0.107 |
| Isobutylene | 0.000 | 0.069 | 92.193 | 0.000 | 0.000 | 92.495 |
| Acetone | 1.255 | 0.065 | 2.410 | 1.167 | 0.144 | 2.465 |
| Isopropanol | 0.320 | 0.661 | 0.046 | 0.306 | 0.688 | 0.036 |
| t-Butyl Alcohol | 94.934 | 61.644 | 1.868 | 95.332 | 59.034 | 1.573 |
| Me-t-Butyl Ether | 0.042 | 0.061 | 2.311 | 0.052 | 0.110 | 1.517 |
| Me Et. Ketone | 0.164 | 1.467 | 0.000 | 0.150 | 0.074 | 0.000 |
| Diisobutylene | 0.039 | 0.000 | 0.000 | 0.000 | 0.000 | 0.000 |
| Unknowns | 1.442 | 0.636 | 0.313 | 1.106 | 1.296 | 0.164 |
| Weight (g) | 1158.0 | 581.0 | 636.0 | 1179.0 | 553.0 | 510.0 |
| Reactor Conditions: | | | | | | |
| Reboiler Temp., (°C.) | 96 | | | 95 | | |
| Column Bottom, Temp., (°C.) | 97 | | | 95 | | |
| Column Top, Temp., (°C.) | 75 | | | 78 | | |
| Reflux Temp., (°C.) | 55 | | | 57 | | |
| Differential Press. (In.) | 0 | | | 0 | | |
| Reactor Press., (psig) | 9.6 | | | 8.2 | | |
| Feed Rate, (g/hr) | 202 | | | 192 | | |
| Time on Stream (Hr) | 6.0 | | | 6.2 | | |
| Catalyst | Valfor CP 861 DL-25 (B-Zeolite) | | | Valfor CP 861 DL-25 (B-Zeolite) | | |
| Material Balance, % | 105.09 | | | 90.16 | | |
| t-Butyl Alcohol Conversion, % | 66.34 | | | 70.24 | | |
| Isobutylene Selectivity, % | 106.30 | | | 78.94 | | |
| Water Selectivity, % | 109.71 | | | 105.88 | | |
| Diisobutylene Selectivity, % | −0.04 | | | 0.00 | | |

TABLE 5-4 tert-Butyl Alcohol Dehydration by Catalytic Distillation

| | 7456-15 | | | 7456-17 | | |
|---|---|---|---|---|---|---|
| | Feed | Bottoms | Traps | Feed | Bottoms | Traps |
| Water | 1.355 | 36.090 | 1.388 | 1.223 | 42.905 | 0.259 |
| Methanol | 0.352 | 0.010 | 0.110 | 0.390 | 0.080 | 0.087 |
| Isobutylene | 0.000 | 0.000 | 93.263 | 0.000 | 0.000 | 89.714 |
| Acetone | 1.280 | 0.807 | 2.299 | 1.518 | 0.029 | 3.483 |
| Isopropanol | 0.328 | 0.000 | 0.031 | 0.370 | 0.531 | 0.067 |
| t-Butyl Alcohol | 94.894 | 61.403 | 1.265 | 94.957 | 55.303 | 3.654 |
| Me-t-Butyl Ether | 0.000 | 0.068 | 1.559 | 0.000 | 0.057 | 2.260 |
| Me Et. Ketone | 0.345 | 0.050 | 0.000 | 0.000 | 0.036 | 0.000 |
| Diisobutylene | 0.000 | 0.051 | 0.000 | 0.000 | 0.000 | 0.065 |
| Unknowns | 1.446 | 1.521 | 0.085 | 1.542 | 1.059 | 0.411 |
| Weight (g) | 1174.0 | 561.0 | 625.0 | 519.0 | 290.0 | 183.0 |
| Reactor Conditions: | | | | | | |
| Reboiler Temp., (°C.) | 96 | | | 81 | | |
| Column Bottom, Temp., (°C.) | 95 | | | 83 | | |
| Column Top, Temp., (°C.) | 78 | | | 76 | | |
| Reflux Temp., (°C.) | 71 | | | 75 | | |
| Differential Press. (In.) | 0 | | | 7 | | |
| Reactor Press., (psig) | 8.1 | | | 0 | | |
| Feed Rate, (g/hr) | 199 | | | 187 | | |
| Time on Stream (Hr) | 6.2 | | | 4.2 | | |
| Catalyst | Valfor CP 861 DL-25 (B-Zeolite) | | | Valfor CP 861 DL-25 (B-Zeolite) | | |
| Material Balance, % | 101.02 | | | 91.14 | | |
| t-Butyl Alcohol Conversion, % | 68.37 | | | 66.10 | | |
| Isobutylene Selectivity, % | 101.11 | | | 66.59 | | |
| Water Selectivity, % | 105.45 | | | 149.72 | | |
| Diisobutylene Selectivity, % | 0.02 | | | 0.02 | | |

TABLE 5-5 tert-Butyl Alcohol Dehydration by Catalytic Distillation

| | 7456-18 | | | 7456-19 | | |
|---|---|---|---|---|---|---|
| | Feed | Bottoms | Traps | Feed | Bottoms | Traps |
| Water | 1.511 | 23.186 | 0.000 | 1.133 | 19.147 | 0.000 |
| Methanol | 0.402 | 0.080 | 0.000 | 0.384 | 0.065 | 0.059 |
| Isobutylene | 0.004 | 0.000 | 85.145 | 0.004 | 0.000 | 89.598 |
| Acetone | 1.550 | 0.153 | 4.499 | 1.524 | 0.052 | 3.380 |
| Isopropanol | 0.367 | 0.529 | 0.068 | 0.365 | 0.481 | 0.070 |
| t-Butyl Alcohol | 94.482 | 74.934 | 3.455 | 95.001 | 79.259 | 4.313 |
| Me-t-Butyl Ether | 0.023 | 0.021 | 5.204 | 0.000 | 0.019 | 1.981 |
| Me Et. Ketone | 0.000 | 0.021 | 0.000 | 0.000 | 0.038 | 0.000 |
| Diisobutylene | 0.066 | 0.107 | 0.122 | 0.048 | 0.000 | 0.000 |
| Unknowns | 1.595 | 0.969 | 1.507 | 1.541 | 1.939 | 0.599 |
| Weight (g) | 728.0 | 379.0 | 200.0 | 712.0 | 491.0 | 174.0 |
| Reactor Conditions: | | | | | | |
| Reboiler Temp., (°C.) | 81 | | | 80 | | |
| Column Bottom, Temp., (°C.) | 83 | | | 80 | | |
| Column Top, Temp., (°C.) | 76 | | | 31 | | |
| Reflux Temp., (°C.) | 74 | | | 30 | | |
| Differential Press. (In.) | 4.5 | | | 0 | | |
| Reactor Press., (psig) | 0 | | | 0 | | |
| Feed Rate, (g/hr) | 100 | | | 198 | | |
| Time on Stream (Hr) | 5.5 | | | 6.0 | | |
| Catalyst | Valfor CP 861 DL-25 (B-Zeolite) | | | Valfor CP 861 DL-25 (B-Zeolite) | | |
| Material Balance, % | 79.53 | | | 93.40 | | |
| t-Butyl Alcohol Conversion, % | 57.71 | | | 41.36 | | |
| Isobutylene Selectivity, % | 56.67 | | | 73.62 | | |
| Water Selectivity, % | 79.68 | | | 126.40 | | |
| Diisobutylene Selectivity, % | 0.03 | | | −0.08 | | |

EXAMPLES 16–31

These examples illustrate the use of an alternative beta zeolite catalyst (from UOP Corp., #9968950001-5, in 1/16" diameter extruded form) where t-butanol conversion levels to 89% (Example 16) are achieved over a range of mild operating conditions.

Data are summarized in tables 6-1 through 6-8.

TABLE 6-1 tert-Butyl Alcohol Dehydration by Catalytic Distillation

| | 7456-28 | | | 7456-29 | | |
|---|---|---|---|---|---|---|
| | Feed | Bottoms | Traps | Feed | Bottoms | Traps |
| Water | 1.196 | 56.776 | 0.000 | 1.342 | 40.659 | 1.878 |
| Methanol | 0.393 | 0.000 | 0.000 | 1.391 | 0.000 | 0.000 |
| Isobutylene | 0.000 | 0.152 | 76.905 | 0.000 | 0.061 | 79.611 |
| Acetone | 0.187 | 0.000 | 0.000 | 0.190 | 0.000 | 0.099 |
| Isopropanol | 1.546 | 0.932 | 8.442 | 1.150 | 0.130 | 6.031 |
| t-Butyl Alcohol | 94.858 | 40.046 | 6.137 | 94.129 | 57.355 | 5.933 |
| Me-t-Butyl Ether | 0.019 | 0.171 | 6.250 | 0.016 | 0.068 | 4.536 |
| Me Et. Ketone | 0.153 | 0.171 | 0.000 | 0.163 | 1.059 | 0.427 |
| Diisobutylene | 0.054 | 0.532 | 0.345 | 0.028 | 0.000 | 0.000 |
| Unknowns | 1.594 | 1.220 | 1.921 | 2.201 | 0.668 | 1.485 |
| Weight (g) | 648.0 | 112.0 | 362.0 | 464.0 | 243.0 | 131.0 |
| Reactor Conditions: | | | | | | |
| Reboiler Temp., (°C.) | 82 | | | 82 | | |
| Column Bottom, Temp., (°C.) | 83 | | | 83 | | |
| Column Top, Temp., (°C.) | 67 | | | 76 | | |
| Reflux Temp., (°C.) | 46 | | | 74 | | |
| Differential Press. (In.) | 9.3 | | | 8.6 | | |
| Reactor Press., (psig) | 0 | | | 0 | | |
| Feed Rate, (g/hr) | 103 | | | 102 | | |
| Time on Stream (Hr) | 6.0 | | | 5.0 | | |
| Catalyst | UOP Beta Zeolite 1/16" (9968950001-5) | | | UOP Beta Zeolite 1/16" (9968950001-5) | | |
| Material Balance, % | 73.15 | | | 80.60 | | |
| t-Butyl Alcohol Conversion, % | 89.09 | | | 66.31 | | |
| Isobutylene Selectivity, % | 67.21 | | | 47.64 | | |
| Water Selectivity, % | 41.95 | | | 135.00 | | |
| Diisobutylene Selectivity, % | 0.18 | | | −0.03 | | |

TABLE 6-2 tert-Butyl Alcohol Dehydration by Catalytic Distillation

| | 7456-30 | | | 7456-31 | | |
|---|---|---|---|---|---|---|
| | Feed | Bottoms | Traps | Feed | Bottoms | Traps |
| Water | 1.089 | 34.010 | 0.578 | 1.247 | 53.312 | 0.449 |
| Methanol | 0.390 | 0.000 | 0.000 | 0.397 | 0.000 | 0.000 |
| Isobutylene | 0.000 | 0.028 | 94.022 | 0.000 | 0.000 | 93.245 |
| Acetone | 0.271 | 0.000 | 0.022 | 0.192 | 0.000 | 0.020 |
| Isopropanol | 2.324 | 0.017 | 1.822 | 1.558 | 0.153 | 2.445 |
| t-Butyl Alcohol | 93.282 | 64.180 | 1.816 | 94.811 | 44.397 | 1.903 |
| Me-t-Butyl Ether | 0.016 | 0.067 | 1.477 | 0.021 | 0.071 | 1.323 |
| Me Et. Ketone | 0.221 | 0.962 | 0.000 | 0.161 | 1.100 | 0.000 |
| Diisobutylene | 0.000 | 0.000 | 0.091 | 0.027 | 0.000 | 0.008 |
| Unknowns | 2.407 | 0.736 | 0.172 | 1.586 | 0.967 | 0.607 |
| Weight (g) | 441.0 | 212.0 | 322.0 | 1174.0 | 569.0 | 580.0 |
| Reactor Conditions: | | | | | | |
| Reboiler Temp., (°C.) | 97 | | | 100 | | |
| Column Bottom, Temp., (°C.) | 96 | | | 100 | | |
| Column Top, Temp., (°C.) | 63 | | | 89 | | |
| Reflux Temp., (°C.) | 35 | | | 56 | | |
| Differential Press. (In.) | 0 | | | 2 | | |
| Reactor Press., (psig) | 9.4 | | | 10.5 | | |
| Feed Rate, (g/hr) | 99 | | | 203 | | |
| Time on Stream (Hr) | 5.2 | | | 6.0 | | |
| Catalyst | UOP Beta Zeolite 1/16" (9968950001-5) | | | UOP Beta Zeolite 1/16" (9968950001-5) | | |
| Material Balance, % | 121.09 | | | 97.97 | | |
| t-Butyl Alcohol Conversion, % | 65.50 | | | 76.31 | | |
| Isobutylene Selectivity, % | 148.47 | | | 84.12 | | |
| Water Selectivity, % | 105.59 | | | 141.09 | | |
| Diisobutylene Selectivity, % | 0.07 | | | −0.02 | | |

TABLE 6-3 tert-Butyl Alcohol Dehydration by Catalytic Distillation

| | 7456-32 | | | 7456-33 | | |
|---|---|---|---|---|---|---|
| | Feed | Bottoms | Traps | Feed | Bottoms | Traps |
| Water | 1.066 | 34.689 | 0.194 | 1.123 | 28.010 | 0.075 |
| Methanol | 0.409 | 0.000 | 0.000 | 0.425 | 0.000 | 0.067 |
| Isobutylene | 0.000 | 0.047 | 92.533 | 0.000 | 0.041 | 91.169 |
| Acetone | 0.202 | 0.000 | 0.047 | 0.186 | 0.000 | 0.015 |
| Isopropanol | 1.691 | 0.036 | 3.410 | 1.759 | 0.044 | 3.971 |
| t-Butyl Alcohol | 94.753 | 62.488 | 1.384 | 94.690 | 69.719 | 2.232 |
| Me-t-Butyl Ether | 0.000 | 0.062 | 2.252 | 0.019 | 0.062 | 1.947 |
| Me Et. Ketone | 0.173 | 1.331 | 0.000 | 0.162 | 0.899 | 0.012 |
| Diisobutylene | 0.000 | 0.265 | 0.000 | 0.057 | 0.250 | 0.029 |
| Unknowns | 1.706 | 1.082 | 0.180 | 1.579 | 0.975 | 0.483 |
| Weight (g) | 1222.0 | 489.0 | 665.0 | 1192.0 | 686.0 | 493.0 |
| Reactor Conditions: | | | | | | |
| Reboiler Temp., (°C.) | 97 | | | 97 | | |
| Column Bottom, Temp., (°C.) | 98 | | | 98 | | |
| Column Top, Temp., (°C.) | 87 | | | 86 | | |
| Reflux Temp., (°C.) | 78 | | | 79 | | |
| Differential Press. (In.) | 0 | | | 0 | | |
| Reactor Press., (psig) | 9.9 | | | 10.8 | | |
| Feed Rate, (g/hr) | 192 | | | 201 | | |
| Time on Stream (Hr) | 6.5 | | | 6.2 | | |
| Catalyst | UOP Beta Zeolite 1/16" (9968950001-5) | | | UOP Beta Zeolite 1/16" (9968950001-5) | | |
| Material Balance, % | 94.44 | | | 98.91 | | |
| t-Butyl Alcohol Conversion, % | 72.82 | | | 56.65 | | |
| Isobutylene Selectivity, % | 96.46 | | | 92.93 | | |
| Water Selectivity, % | 77.05 | | | 115.25 | | |
| Diisobutylene Selectivity, % | 0.10 | | | 0.12 | | |

TABLE 6-4 tert-Butyl Alcohol Dehydration by Catalytic Distillation

| | 7456-34 | | | 7456-35 | | |
|---|---|---|---|---|---|---|
| | Feed | Bottoms | Traps | Feed | Bottoms | Traps |
| Water | 1.117 | 29.145 | 0.127 | 1.182 | 29.422 | 0.114 |
| Methanol | 0.443 | 0.000 | 0.215 | 0.439 | 0.000 | 0.225 |
| Isobutylene | 0.000 | 0.018 | 87.969 | 0.000 | 0.000 | 89.814 |
| Acetone | 0.187 | 0.000 | 0.000 | 0.184 | 0.000 | 0.000 |
| Isopropanol | 1.733 | 0.135 | 3.357 | 1.744 | 0.254 | 0.000 |
| t-Butyl Alcohol | 94.572 | 68.154 | 2.662 | 94.584 | 67.415 | 3.451 |
| Me-t-Butyl Ether | 0.020 | 0.019 | 1.571 | 0.021 | 0.213 | 1.153 |
| Me Et. Ketone | 0.225 | 1.053 | 0.000 | 0.021 | 0.987 | 0.000 |
| Diisobutylene | 0.062 | 0.271 | 3.823 | 0.084 | 0.178 | 1.688 |
| Unknowns | 1.641 | 1.205 | 0.276 | 1.741 | 1.531 | 3.555 |
| Weight (g) | 1076.0 | 682.0 | 408.0 | 1091.0 | 463.0 | 404.0 |
| Reactor Conditions: | | | | | | |
| Reboiler Temp., (°C.) | 115 | | | 115 | | |
| Column Bottom, Temp., (°C.) | 112 | | | 112 | | |
| Column Top, Temp., (°C.) | 101 | | | 99 | | |
| Reflux Temp., (°C.) | 68 | | | 54 | | |
| Differential Press. (In.) | 6.1 | | | 4.9 | | |
| Reactor Press., (psig) | 29.7 | | | 30.2 | | |
| Feed Rate, (g/hr) | 195 | | | 196 | | |
| Time on Stream (Hr) | 5.5 | | | 6.0 | | |
| Catalyst | UOP Beta Zeolite 1/16" (9968950001-5) | | | UOP Beta Zeolite 1/16" (9968950001-5) | | |
| Material Balance, % | 101.30 | | | 79.47 | | |
| t-Butyl Alcohol Conversion, % | 53.26 | | | 68.40 | | |
| Isobutylene Selectivity, % | 87.53 | | | 67.92 | | |
| Water Selectivity, % | 142.17 | | | 72.15 | | |
| Diisobutylene Selectivity, % | 2.05 | | | 0.63 | | |

TABLE 6-5 tert-Butyl Alcohol Dehydration by Catalytic Distillation

| | 7456-37 | | | 7456-38 | | |
|---|---|---|---|---|---|---|
| | Feed | Bottoms | Traps | Feed | Bottoms | Traps |
| Water | 1.175 | 59.313 | 0.865 | 1.173 | 45.244 | 0.186 |
| Methanol | 0.419 | 0.000 | 0.139 | 0.429 | 0.000 | 0.000 |
| Isobutylene | 0.000 | 0.088 | 94.240 | 0.000 | 0.085 | 94.862 |
| Acetone | 0.167 | 0.000 | 0.010 | 0.174 | 0.000 | 0.000 |
| Isopropanol | 1.703 | 0.244 | 2.141 | 1.713 | 0.170 | 2.428 |
| t-Butyl Alcohol | 94.699 | 37.750 | 1.308 | 94.640 | 52.470 | 1.521 |
| Me-t-Butyl Ether | 0.020 | 0.082 | 1.208 | 0.020 | 0.044 | 0.771 |
| Me Et. Ketone | 0.162 | 1.150 | 0.000 | 0.165 | 0.994 | 0.004 |
| Diisobutylene | 0.053 | 0.339 | 0.000 | 0.058 | 0.000 | 0.000 |
| Unknowns | 1.602 | 1.034 | 0.089 | 1.628 | 0.993 | 0.228 |
| Weight (g) | 1193.0 | 392.0 | 837.0 | 1096.0 | 430.0 | 467.0 |
| Reactor Conditions: | | | | | | |
| Reboiler Temp., (°C.) | 108 | | | 107 | | |
| Column Bottom, Temp., (°C.) | 107 | | | 105 | | |
| Column Top, Temp., (°C.) | 89 | | | 68 | | |
| Reflux Temp., (°C.) | 75 | | | 46 | | |
| Differential Press. (In.) | 0 | | | 1.3 | | |
| Reactor Press., (psig) | 20.7 | | | 20.4 | | |
| Feed Rate, (g/hr) | 199 | | | 200 | | |
| Time on Stream (Hr) | 6.0 | | | 5.0 | | |
| Catalyst | UOP Beta Zeolite 1/16" (9968950001-5) | | | UOP Beta Zeolite 1/16" (9968950001-5) | | |
| Material Balance, % | 103.02 | | | 81.84 | | |
| t-Butyl Alcohol Conversion, % | 85.93 | | | 77.56 | | |
| Isobutylene Selectivity, % | 107.39 | | | 72.81 | | |
| Water Selectivity, % | 95.66 | | | 93.36 | | |
| Diisobutylene Selectivity, % | 0.05 | | | −0.05 | | |

TABLE 6-6 tert-Butyl Alcohol Dehydration by Catalytic Distillation

| | 7456-39 | | | 7456-41 | | |
|---|---|---|---|---|---|---|
| | Feed | Bottoms | Traps | Feed | Bottoms | Traps |
| Water | 1.123 | 39.144 | 0.103 | 1.158 | 66.315 | 0.055 |
| Methanol | 0.427 | 0.000 | 0.000 | 0.432 | 0.000 | 0.000 |
| Isobutylene | 0.000 | 0.038 | 92.814 | 0.000 | 0.023 | 96.217 |
| Acetone | 0.178 | 0.000 | 0.026 | 0.174 | 0.000 | 0.000 |
| Isopropanol | 1.760 | 0.219 | 3.451 | 1.714 | 0.161 | 2.246 |
| t-Butyl Alcohol | 94.723 | 57.285 | 1.808 | 94.662 | 30.448 | 0.542 |
| Me-t-Butyl Ether | 0.018 | 0.111 | 1.418 | 0.020 | 0.102 | 0.700 |
| Me Et. Ketone | 0.159 | 1.399 | 0.008 | 0.162 | 1.125 | 0.000 |
| Diisobutylene | 0.000 | 0.291 | 0.000 | 0.060 | 0.487 | 0.000 |
| Unknowns | 1.612 | 1.513 | 0.372 | 1.618 | 1.339 | 0.240 |
| Weight (g) | 994.0 | 437.0 | 545.0 | 1090.0 | 585.0 | 621.0 |
| Reactor Conditions: | | | | | | |
| Reboiler Temp., (°C.) | 106 | | | 108 | | |
| Column Bottom, Temp., (°C.) | 104 | | | 107 | | |
| Column Top, Temp., (°C.) | 89 | | | 85 | | |
| Reflux Temp., (°C.) | 79 | | | 71 | | |
| Differential Press. (In.) | 3.9 | | | 0 | | |
| Reactor Press., (psig) | 19.8 | | | 21.8 | | |
| Feed Rate, (g/hr) | 202 | | | 197 | | |
| Time on Stream (Hr) | 5.0 | | | 5.5 | | |
| Catalyst | UOP Beta Zeolite 1/16" (9968950001-5) | | | UOP Beta Zeolite 1/16" (9968950001-5) | | |
| Material Balance, % | 98.79 | | | 110.64 | | |
| t-Butyl Alcohol Conversion, % | 72.37 | | | 82.41 | | |
| Isobutylene Selectivity, % | 98.12 | | | 92.86 | | |
| Water Selectivity, % | 96.89 | | | 181.76 | | |
| Diisobutylene Selectivity, % | 0.12 | | | 0.17 | | |

TABLE 6-7 tert-Butyl Alcohol Dehydration by Catalytic Distillation

|  | 7456-42 | | | 7456-43 | | |
| --- | --- | --- | --- | --- | --- | --- |
|  | Feed | Bottoms | Traps | Feed | Bottoms | Traps |
| Water | 1.013 | 38.921 | 0.039 | 1.012 | 33.804 | 0.050 |
| Methanol | 0.445 | 0.000 | 0.000 | 0.450 | 0.224 | 0.000 |
| Isobutylene | 0.000 | 0.050 | 96.761 | 0.000 | 0.000 | 96.182 |
| Acetone | 0.181 | 0.000 | 0.000 | 0.169 | 0.000 | 0.000 |
| Isopropanol | 1.722 | 0.176 | 2.009 | 1.708 | 0.493 | 1.852 |
| t-Butyl Alcohol | 94.762 | 58.205 | 0.458 | 94.809 | 62.976 | 1.217 |
| Me-t-Butyl Ether | 0.014 | 0.196 | 0.554 | 0.019 | 0.150 | 0.436 |
| Me Et. Ketone | 0.167 | 1.188 | 0.000 | 0.211 | 1.079 | 0.000 |
| Diisobutylene | 0.057 | 0.000 | 0.000 | 0.000 | 0.000 | 0.000 |
| Unknowns | 1.639 | 1.264 | 0.179 | 1.622 | 1.274 | 0.263 |
| Weight (g) | 1045.0 | 438.0 | 574.0 | 1132.0 | 533.0 | 544.0 |
| Reactor Conditions: | | | | | | |
| Reboiler Temp., (°C.) | 108 | | | 107 | | |
| Column Bottom, Temp., (°C.) | 106 | | | 106 | | |
| Column Top, Temp., (°C.) | 65 | | | 87 | | |
| Reflux Temp., (°C.) | 40 | | | 79 | | |
| Differential Press. (In.) | 0 | | | 5.2 | | |
| Reactor Press., (psig) | 21.6 | | | 20.4 | | |
| Feed Rate, (g/hr) | 196 | | | 193 | | |
| Time on Stream (Hr) | 5.0 | | | 6.0 | | |
| Catalyst | UOP Beta Zeolite 1/16" (9968950001-5) | | | UOP Beta Zeolite 1/16" (9968950001-5) | | |
| Material Balance, % | 96.84 | | | 95.14 | | |
| t-Butyl Alcohol Conversion, % | 73.99 | | | 68.11 | | |
| Isobutylene Selectivity, % | 100.19 | | | 94.57 | | |
| Water Selectivity, % | 89.90 | | | 95.12 | | |
| Diisobutylene Selectivity, % | −0.05 | | | 0.00 | | |

TABLE 6-8 tert-Butyl Alcohol Dehydration by Catalytic Distillation

|  | 7456-44 | | | 7456-48 | | |
| --- | --- | --- | --- | --- | --- | --- |
|  | Feed | Bottoms | Traps | Feed | Bottoms | Traps |
| Water | 1.064 | 23.211 | 0.020 | 1.029 | 12.737 | 0.251 |
| Methanol | 0.457 | 0.000 | 0.000 | 0.452 | 0.190 | 0.000 |
| Isobutylene | 0.000 | 0.179 | 94.908 | 0.000 | 4.630 | 94.899 |
| Acetone | 1.549 | 0.000 | 3.353 | 1.792 | 0.986 | 1.782 |
| Isopropanol | 0.384 | 0.661 | 0.000 | 0.340 | 0.295 | 0.096 |
| t-Butyl Alcohol | 95.010 | 74.546 | 0.153 | 94.861 | 80.737 | 2.464 |
| Me-t-Butyl Ether | 0.000 | 0.021 | 1.346 | 0.000 | 0.000 | 0.355 |
| Me Et. Ketone | 0.162 | 0.268 | 0.000 | 0.167 | 0.082 | 0.000 |
| Diisobutylene | 0.000 | 0.000 | 0.000 | 0.000 | 0.000 | 0.000 |
| Unknowns | 1.374 | 1.114 | 0.220 | 1.359 | 0.343 | 0.153 |
| Weight (g) | 1119.0 | 724.0 | 363.0 | 442.0 | 333.0 | 59.0 |
| Reactor Conditions: | | | | | | |
| Reboiler Temp., (°C.) | 107 | | | 96 | | |
| Column Bottom, Temp., (°C.) | 106 | | | 43 | | |
| Column Top, Temp., (°C.) | 70 | | | 27 | | |
| Reflux Temp., (°C.) | 46 | | | 23 | | |
| Differential Press. (In.) | 0 | | | 0 | | |
| Reactor Press., (psig) | 20.7 | | | 10.3 | | |
| Feed Rate, (g/hr) | 195 | | | 104 | | |
| Time on Stream (Hr) | 6.0 | | | 4.5 | | |
| Catalyst | UOP Beta Zeolite 1/16" (9968950001-5) | | | Dow Superacid (Alumina Support) | | |
| Material Balance, % | 97.14 | | | 88.69 | | |
| t-Butyl Alcohol Conversion, % | 49.18 | | | 35.53 | | |
| Isobutylene Selectivity, % | 87.38 | | | 63.33 | | |
| Water Selectivity, % | 122.91 | | | 104.98 | | |
| Diisobutylene Selectivity, % | 0.00 | | | 0.00 | | |

What is claimed is:

1. A method for the dehydration of a tertiary butyl alcohol (TBA) feedstock in a reactive distillation column having a reactive distillation section in the middle portion thereof containing a bed of a TBA dehydration catalyst to form isobutylene and water which comprises:

charging a tertiary butyl alcohol feedstock to the middle reactive distillation section of a reactive distillation column containing a bed of a catalyst under reactive distillation conditions effective for the separation of the isobutylene and to provide a lower boiling isobutylene-containing fraction for upward flow into the upper portion of the reactive distillation column and to provide a higher boiling water fraction for downward flow into the lower portion of the reactive distillation column and recovering a substantially anhydrous lower boiling isobutylene fraction adjacent the top of said extractive distillation column and a higher boiling aqueous fraction adjacent the bottom of said extractive distillation column, said distillation conditions in the reactive distillation column including a reaction column temperature of about 30° to about 150° C., a reboiler temperature of about 50° to about 180° C. and a pressure of about zero to about 500 psi said catalyst being selected from the group consisting of fluoride-treated beta zeolite catalyst and flouride-treated montmorillonite clay catalyst.

2. A method as in claim 1 wherein the catalyst is a fluoride-treated beta zeolite catalyst and wherein the reaction conditions in the reactive distillation column include a reaction column temperature of about 60° to about 120° C., a reboiler temperature of about 70° to about 140° C., and a pressure of about 5 to 30 psi.

3. A method as in claim 2 wherein said beta zeolite has a silica-to-alumina ratio in the range of 20:1 to 100:1.

4. A method as in claim 2 wherein the fluoride-treating agent is taken from the group including hydrogen fluoride and hydrofluoric acid.

5. A method as in claim 2 wherein said flouride-treated beta zeolite has a fluoride content in the range of 0.1 to 10%.

6. A method as in claim 1 wherein said catalyst is a fluoride-treated montmorillonite clay catalyst and wherein the reaction conditions in the reactive distillation column include a reaction column temperature of about 60° to about 120° C., a reboiler temperature of about 70° to about 140° C. and a pressure of about 5 to 30 psi.

7. A method as in claim 6 wherein the fluoride-treating agent is taken from the group including hydrogen fluoride and hydrofluoric acid.

8. A method as in claim 6 wherein said flouride-treated montmorillionite clay catalyst has a fluoride content in the range of 0.2 to 2%.

* * * * *